United States Patent [19]

Shimizu et al.

[11] Patent Number: 4,604,492
[45] Date of Patent: Aug. 5, 1986

[54] DICYCLOHEXYLCYCLOPENTANE COMPOUNDS

[75] Inventors: Nobuaki Shimizu; Toshiyuki Tsubouchi, both of Sodegaura; Hitoshi Hata, Ichihara, all of Japan

[73] Assignee: Idemitsu Kosan Company Limited, Tokyo, Japan

[21] Appl. No.: 785,458

[22] Filed: Oct. 8, 1985

[30] Foreign Application Priority Data

Oct. 23, 1984 [JP] Japan .................................. 59-221182

[51] Int. Cl.$^4$ ............................................. C07C 13/28
[52] U.S. Cl. ...................................... 585/360; 208/14; 252/73; 585/20; 585/21; 585/22; 585/269; 585/270; 585/516
[58] Field of Search ...................... 208/14; 252/73, 9; 585/20, 21, 22, 23, 360, 361, 516, 269, 270

[56] References Cited

U.S. PATENT DOCUMENTS 4,521,324  6/1985  Tsubouchi et al. ................. 585/360
4,525,290  6/1985  Tsubouchi et al. ................. 585/360
4,556,503 12/1985  Tsubouchi et al. ................. 585/360

Primary Examiner—Andrew H. Metz
Assistant Examiner—A. Pal
Attorney, Agent, or Firm—Frishauf, Holtz, Goodman & Woodward

[57] ABSTRACT

The invention provides a novel class of compounds dicyclohexylcyclopentanes or, in particular, 1,3-dicyclohexyl-1-methyl cyclopentane which is synthesized by the hydrogenation of 1-methyl-1,3-diphenyl cyclopentane which in turn is obtained by the dimerization reaction of α-methylstyrene in the presence of metallic sodium as the catalyst. The compound is useful as a fluid for traction drive.

5 Claims, 2 Drawing Figures

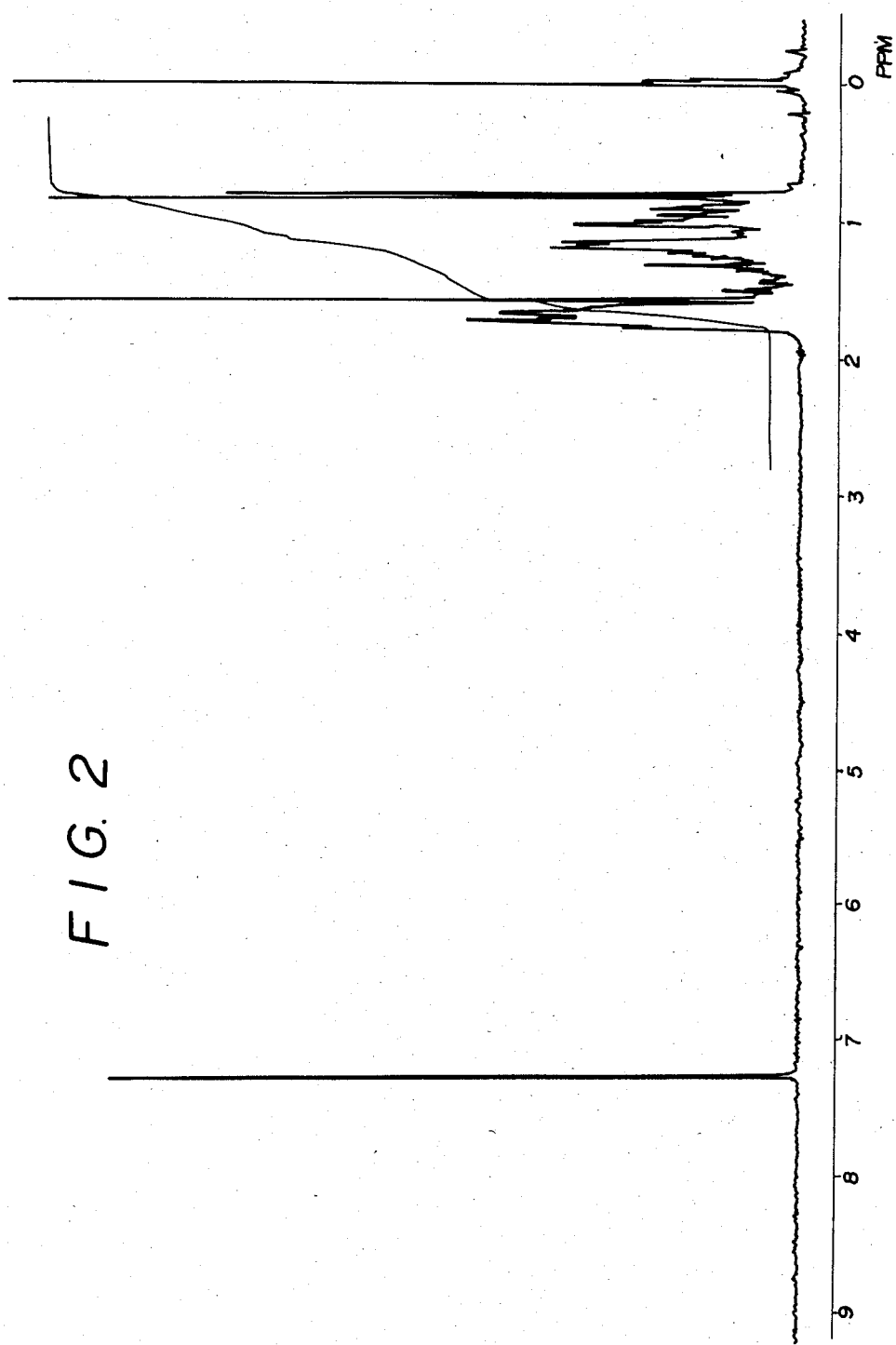

DICYCLOHEXYLCYCLOPENTANE COMPOUNDS

BACKGROUND OF THE INVENTION

The present invention relates to a novel compound dicyclohexylcyclopentane, and more particularly, it is concerned with a dicyclohexylcyclopentane compound useful for traction drive fluids.

Generally speaking, a working fluid for traction drive is a fluid used in apparatuses of traction drive, i.e. friction drive apparatuses by rolling contact, such as a continuously variable transmission, and the like. When a fluid for traction drive is used in a high-performance traction drive apparatus, the fluid is required to have a high traction coefficient and stability against heat and oxidation along with inexpensiveness as a matter of course.

In recent years, various types of compounds have been proposed as a fluid for traction drive including various polycyclic naphthenic compounds such as those disclosed in Japanese Patent Publication Nos. 338/1971, 339/1971, 35763/1972, 42067/1973, 42068/1973 and 36105/1978 and Japanese Patent Nos. Kokai 43108/1980 and 40726/1980.

These compounds, however, have a relatively high viscosity and cannot be free from the problems of a low efficiency of power transmission due to agitation loss and a limitation in the serviceable range of temperature due to the large temperature dependency of the traction coefficient. Moreover, conventional compounds are not satisfactory for the purpose since a fluid for traction drive is sometimes used at a high temperature of up to 120° to 140° C.

SUMMARY OF THE INVENTION

Thus, the present invention provides a dicyclohexylcyclopentane compound represented by the general formula

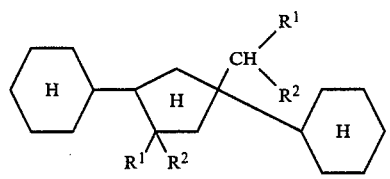
(I)

in which $R^1$ and $R^2$ are each a hydrogen atom or an alkyl group having 1 to 3 carbon atoms.

BRIEF DESCRIPTION OF THE DRAWING

FIG. 2 is a proton nuclear magnetic resonance (NMR) spectrum of the same compound.

DETAILED DESCRIPTION OF THE PREFERRED EMBODIMENTS

Figure 1:
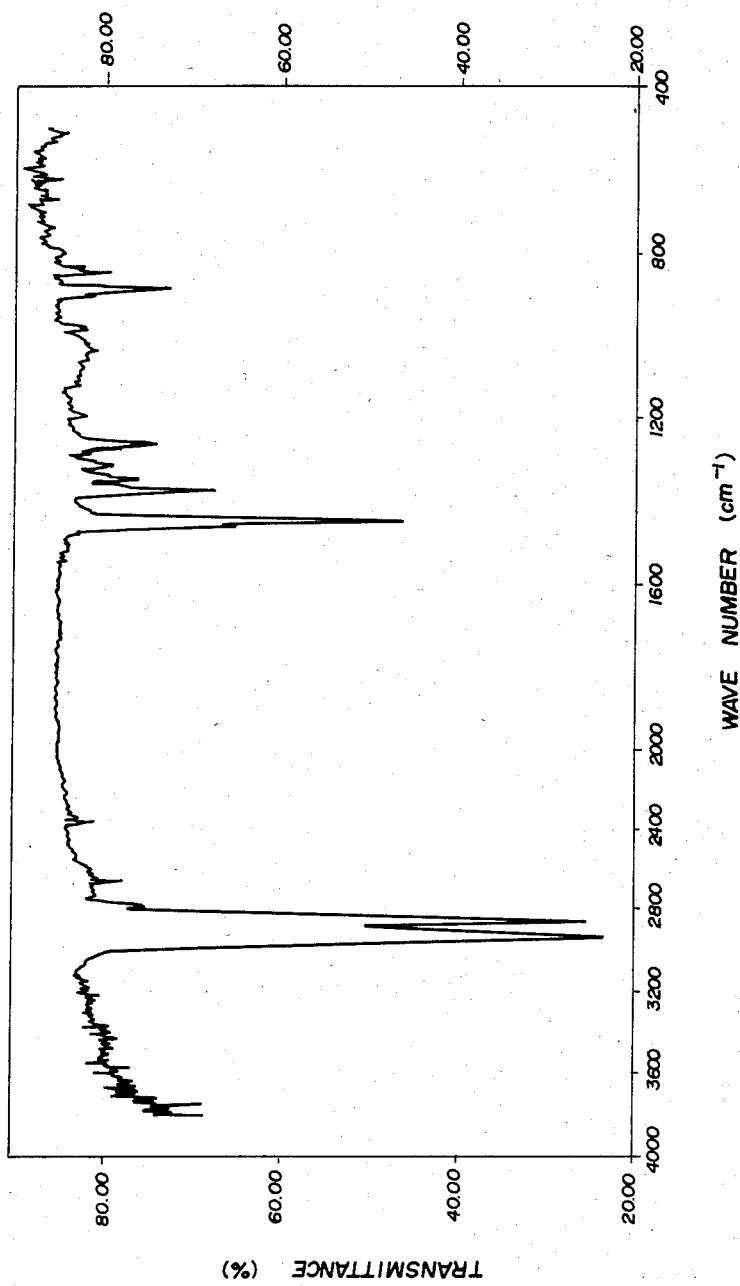
FIG. 1 is an infrared absorption spectrum of 1,3-dicyclohexyl-1-methyl cyclopentane prepared in Example 2.

The dicyclohexylcyclopentane compounds of the present invention belong to a class of novel compounds not known or not described in any prior art literatures and represented by the above given general formula (I). In the formula, the symbols $R^1$ and $R^2$ each denote a hydrogen atom or an alkyl group having from 1 to 3 carbon atoms including methyl, ethyl, n-propyl and isopropyl groups.

Several of the particular examples of the inventive dicyclohexylcyclopentane compounds of the general formula (I) include: 1,3-dicyclohexyl-1-methyl cyclopentane obtained by the substitution of a hydrogen atom for each of the groups of $R^1$ and $R^2$ in the general formula (I) and expressed by the structural formula

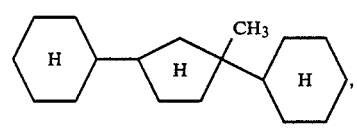
(II)

1-ethyl-1,3-dicyclohexyl-4-methyl cyclopentane obtained by the substitution of a methyl group and a hydrogen atom for each of the groups $R^1$ and for each of the groups $R^2$, respectively, in the general formula (I) and expressed by the structural formula

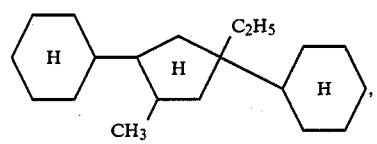
(III)

1,3-dicyclohexyl-4,4-dimethyl-1-isopropyl cyclopentane obtained by the substitution of a methyl group for each of the groups $R^1$ and $R^2$ in the general formula and expressed by the structural formula

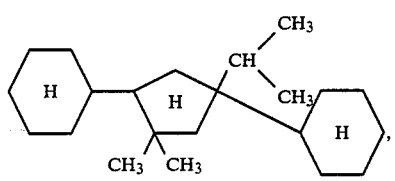
(IV)

and 4-ethyl-1,3-dicyclohexyl-1-n-propyl cyclopentane obtained by the substitution of an ethyl group and a hydrogen atom for each of the groups $R^1$ and for each of the groups $R^2$, respectively, in the general formula (I) and expressed by the structural formula

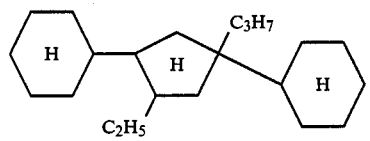
(V)

The dicyclohexylcyclopentane compounds of the invention represented by the general formula (I) can be prepared in several different synthetic routes but a convenient and efficient synthetic method is the hydrogenation of a 1,3-diphenylcyclopentane compound which in turn is obtained by the dimerization of an α-alkylstyrene of which the alkyl groups has 1 to 3 carbon atoms.

The above mentioned dimerization reaction of an α-alkylstyrene proceeds according to the following reaction equation

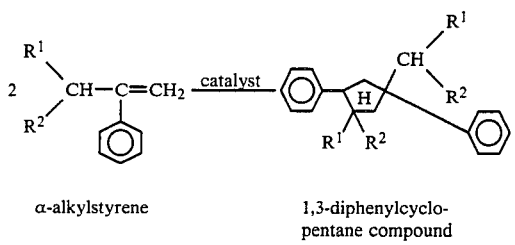

α-alkylstyrene     1,3-diphenylcyclo-
                   pentane compound and the reaction is accelerated by a catalyst such as metallic sodium or a combination of metallic sodium with 2-chlorotoluene or potassium hydroxide. The combination of metallic sodium and potassium hydroxide is particularly preferable. In this case, the metallic sodium is used in an amount preferably in the range from 0.05 to 20% by weight based on the starting α-alkylstyrene while potassium hydroxide is used in an amount preferably in the range from 5 to 100% by weight based on the metallic sodium. When 2-chlorotoluene is used in combination with metallic sodium, on the other hand, the 2-chlorotoluene is used in an amount preferably in the range from 10 to 200% by weight based on the metallic sodium.

The dimerization reaction of the α-alkylstyrene can proceed even in the absence of any solvent but it is preferably undertaken in an organic solvent. Suitable solvents therefor are exemplified by paraffins and cycloparaffins having a boiling point of 80° C. or higher such as decane, decahydronaphthalene and the like and aromatic hydrocarbons such as cumene and the like.

The thus obtained 1,3-diphenylcyclopentane compound is then hydrogenated according to the following reaction equation to give the desired dicyclohexylcyclopentane compound:

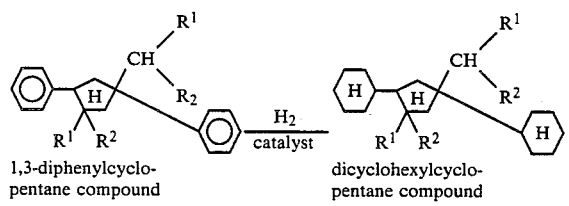

1,3-diphenylcyclo-        dicyclohexylcyclo-
pentane compound          pentane compound The reaction conditions for the hydrogenation are not particularly limitative but usually the reaction can readily proceed at a temperature in the range from 20° to 250° C. under a hydrogen pressure of 5 to 100 atmospheres in the presence of a catalyst containing an active ingredient such as nickel, platinum, palladium, ruthenium, rhodium, iridium and the like. The hydrogenation reaction can be performed either by using a suitable solvent or without using any solvent.

Dicyclohexylcyclopentane compounds obtained in this manner are novel compounds and, as mentioned above, useful for traction drive fluids. These compounds are chemically stable and odorless so that they are also useful as high-boiling solvents and in many applications as a synthetic functional fluid such as working fluids, lubricant oils and the like.

In the following, the present invention is described in more detail by way of examples.

PREPARATION

Into a four-necked glass flask of 1-liter capacity equipped with a stirrer, dropping funnel, reflux condenser with a calcium chloride tube, thermometer and bifurcated gas inlet tube were introduced 200 ml of decahydronaphthalene, 9.2 g (0.40 mole) of metallic sodium and 11.2 g (0.20 mole) of potassium hydroxide to form a reaction mixture which was agitated with introduction of argon gas through the gas inlet tube at a rate of 100 ml/minute for the first 10 minutes and then at a reduced rate of 10 ml/minute. Thereafter, the reaction mixture was heated at 135° C. on an oil bath and 473 g (4.0 moles) of α-methylstyrene were added dropwise thereinto through the dropping funnel over a period of 1 hour. After completion of the dropwise addition of α-methylstyrene, heating and agitation of the reaction mixture were continued for further 30 minutes. The reaction mixture was cooled to room temperature and 100 ml of methyl alcohol were added dropwise thereinto to deactivate the unreacted metallic sodium. Introduction of argon gas was interrupted and the reaction mixture was washed three times each with 200 ml of water. The thus washed reaction mixture was dried over anhydrous sodium sulfate and subjected to distillation under reduced pressure to give 250.7 g of a fraction boiling at 139° to 141° C. under a pressure of 0.2 mmHg. This product was analyzed by the gas chromatography-mass spectrometric analysis, proton NMR spectrometric analysis, $^{13}$C NMR spectrometric analysis and infrared absorption spectrophotometry and identified to be 1-methyl-1,3-diphenyl cyclopentane. The product had a purity of 82% as determined by the gas chromatography with FID.

EXAMPLE 1

Into a stainless steel-made autoclave of 1-liter capacity equipped with an electromagnetic stirrer were introduced 200 g (0.85 mole) of the 2-methyl-1,3-diphenyl cyclopentane of 82% purity obtained in the above described Preparation and 10 g of a nickel catalyst (N-113, a product by Nikki Kagaku Co.) and the hydrogenation reaction was performed at 150° C. for 2 hours under a hydrogen pressure of 20 atmospheres. After completion of the reaction, the catalyst was separated from the reaction mixture by filtration and washed with xylene to give a washing which was combined with the filtrate from the reaction mixture. The reaction mixture was freed from the xylene by evaporation in a rotary evaporator to give 206 g of a product having a purity of 82% which could be identified to be 1,3-dicyclohexyl-1-methyl cyclopentane. The above mentioned yield was 98% of the theoretical value. The physical properties of this product were as shown below. The purity thereof was determined by the gas chromatography with FID.

(1) Refractive index: $n_D^{20} = 1.4964$.

(2) Specific gravity: $d_4^{15} = 0.8904$.

(3) Kinematic viscosity: 21.2 cSt at 40° C. and 3.80 cSt at 100° C.

(4) Viscosity index: 38 (according to JIS K 2284).

(5) Fluidity point: −35° C. or below (according to JIS K 2269).

(6) Distillation behavior: 326.5° C. (temperature for 50% distillation according to JIS K 2254).

EXAMPLE 2

The 1,3-dicyclohexyl-1-methyl cyclopentane product of 82% purity obtained in Example 1 was upgraded by subjecting 200 mg of the product to high-performance liquid chromatography to give 85 mg of a purified product of 1,3-dicyclohexyl-1-methyl cyclopentane having a purity of 96% as determined by the gas chromatography with FID. This product was identified to be the desired 1,3-dicyclohexyl-1-methyl cyclopentane by the elementary analysis, gas chromatography-mass spectrometric analysis, infrared absorption spectrophotometry and proton NMR spectrometric analysis to give the results shown below including the refractive index.

(1) Elementary analysis: Found: C 87.0% and H 13.0%. Calculated as $C_{18}H_{32}$: C 86.9% and H 13.1%.

(2) Refractive index: $n_D^{20} = 1.4967$.

(3) Infrared absorption spectrum: see FIG. 1 (taken with a Fourier-transformation infrared spectrophotometer Model JIR 40X manufactured by Nippon Denshi Co.).

(4) Proton NMR spectrum: see FIG. 2 (taken with a NMR spectrometer Model GX-270 manufactured by Nippon Denshi Co.).

EXAMPLE 3

The compound prepared in Example 2 was subjected to the determination of the traction coefficient to give values of 0.075 and 0.067 at temperatures of 120° C. and 140° C., respectively.

The traction coefficient was determined in the following procedure using a two roller machine. Namely, two rollers having the same dimensions of 60 mm diameter and 6 mm height and contacting with each other were rotated each at a constant velocity of, one, 2000 r.p.m. and, the other, 1700 r.p.m. under a load of 140 kg on the contacting line given by a spring and the torque was determined by use of a strain gage and a torquemeter to calculate the traction coefficient. The rollers were made of a carbon steel SCM-3 and the surface thereof was finished by buffing using an alumina abrasive of 0.03 μm particle diameter to have a surface roughness $R_{max}$ of 0.2 μm. The Herzian contact pressure was 75 kg/mm². The measurement was performed by controlling the temperature of the oil in the oil tank heated with a heater.

COMPARATIVE EXAMPLE 1

Into a glass-made flask of 3-liter capacity were introduced 1000 g of α-methylstyrene, 50 g of acid clay and 50 g of ethylene glycol and the mixture was agitated at 140° C. for 2 hours to effect the reaction. After completion of the reaction, the reaction mixture was filtered to remove the acid clay as the catalyst and the filtrate was subjected to distillation to give 900 g of a fraction boiling at 125° to 130° C. under a pressure of 0.2 mmHg after stripping of the unreacted α-methylstyrene and ethylene glycol. The thus obtained fraction was identified to be a mixture of 95% by weight and 5% by weight of a linear dimer and a cyclic dimer, respectively, of α-methylstyrene from the results of the NMR and gas chromatography analyses.

The fraction was subjected to a post-treatment of hydrogenation in the same manner as in Example 1 to give a fluid for traction drive mainly composed of 2,4-dicyclohexyl-2-methyl pentane. The fluid had a specific gravity $d_4^{15}$ of 0.90, kinematic viscosity of 22 cSt at 40° C. and 3.7 cSt at 100° C. and viscosity index of 16.

The fluid was further subjected to the determination of the traction coefficient in the same manner as in Example 3 to give values of 0.070 and 0.059 at temperatures of 120° C. and 140° C., respectively. This result indicates that the traction coefficient of the fluid prepared in this comparative example is definitely lower than that of the inventive compounds despite the same starting material of α-methylstyrene used in the preparation of them.

What is claimed is:

1. A dicyclohexylcyclopentane compound represented by the general formula

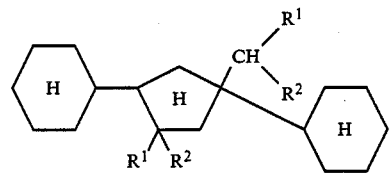

in which $R^1$ and $R^2$ are each a hydrogen atom or an alkyl group having from 1 to 3 carbon atoms.

2. The dicyclohexylcyclopentane compound as claimed in claim 1, wherein the groups denoted by $R^1$ and $R^2$ are each a hydrogen atom.

3. A fluid for traction drive which comprises a dicyclohexylcyclopentane compound of claim 1.

4. A process for improving the coefficient of traction between at least two relatively rotatable elements in a torque transmitting relationship and for maintaining said coefficient of traction at a high level at operating temperatures up to 120°–140° C. which comprises introducing between the tractive surfaces of said elements a traction drive fluid which comprises a dicyclohexylcyclopentane compound represented by the general formula

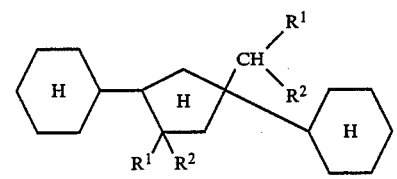

in which $R^1$ and $R^2$ are each a hydrogen atom or an alkyl group having from 1 to 3 carbon atoms.

5. The process of claim 4, wherein the groups denoted by $R^1$ and $R^2$ are each a hydrogen atom.

* * * * *